United States Patent
Feng et al.

(10) Patent No.: US 10,556,981 B2
(45) Date of Patent: Feb. 11, 2020

(54) PHOTOSTABLE COMPOSITIONS COMPRISING PARA-ALKOXYL PHENYL SUBSTITUTED PROPENOIC ACID (APP) COPOLYMER DERIVATIVES

(71) Applicant: HALLSTAR INNOVATIONS CORP., Chicago, IL (US)

(72) Inventors: Hui Feng, Suzhou (CN); Shengkui Hu, Darien, IL (US); Dennis Zlotnik, Chicago, IL (US)

(73) Assignee: Hallstar Beauty and Personal Care Innovations Company, Chicago, IL (US)

( * ) Notice: Subject to any disclaimer, the term of this patent is extended or adjusted under 35 U.S.C. 154(b) by 65 days.

(21) Appl. No.: 15/644,611

(22) Filed: Jul. 7, 2017

(65) Prior Publication Data

US 2018/0009923 A1    Jan. 11, 2018

Related U.S. Application Data

(60) Provisional application No. 62/359,539, filed on Jul. 7, 2016.

(51) Int. Cl.
| | |
|---|---|
| *C08F 293/00* | (2006.01) |
| *C09D 7/65* | (2018.01) |
| *C09D 7/63* | (2018.01) |
| *A61K 8/35* | (2006.01) |
| *A61K 8/37* | (2006.01) |
| *A61K 8/90* | (2006.01) |
| *A61Q 17/04* | (2006.01) |

(52) U.S. Cl.
CPC .............. *C08F 293/00* (2013.01); *A61K 8/35* (2013.01); *A61K 8/37* (2013.01); *A61K 8/90* (2013.01); *A61Q 17/04* (2013.01); *C09D 7/63* (2018.01); *C09D 7/65* (2018.01); *A61K 2800/52* (2013.01)

(58) Field of Classification Search
CPC ..................................... A61Q 7/04; A61K 8/90
See application file for complete search history.

(56) References Cited

U.S. PATENT DOCUMENTS

| | | |
|---|---|---|
| 2011/0250248 A1 | 10/2011 | Omura et al. |
| 2012/0183480 A1 | 7/2012 | Nagare et al. |

FOREIGN PATENT DOCUMENTS

| | | |
|---|---|---|
| JP | 63-172729 A | 7/1998 |
| JP | 2013199596 A | 10/2013 |
| WO | 96-29302 A1 | 9/1996 |

OTHER PUBLICATIONS

International Search Report for PCT/US2017/041232, dated Oct. 19, 2017, 3 pages.
Written Opinion for PCT/US2017-041232, dated Oct. 19, 2017, 7 pages.

*Primary Examiner* — Kyle A Purdy
(74) *Attorney, Agent, or Firm* — Baker & McKenzie LLP

(57) ABSTRACT

The present disclosure relates, according to some embodiments, to photostable photoactive compositions comprising (a) at least one photoactive compound that develops within itself an excited state energy when subjected to UV radiation and (b) a block copolymer comprising a plurality of blocks, wherein the block copolymer is operable to quench the excited state energy.

37 Claims, 7 Drawing Sheets

PHOTOSTABLE COMPOSITIONS COMPRISING PARA-ALKOXYL PHENYL SUBSTITUTED PROPENOIC ACID (APP) COPOLYMER DERIVATIVES

CROSS-REFERENCE TO RELATED APPLICATIONS

This application claims priority to U.S. Application No. 62/359,539, filed Jul. 7, 2016, which is incorporated by reference in its entirety by reference.

FIELD OF THE DISCLOSURE

The present disclosure relates to photostable photoactive compositions comprising para-alkoxyl phenyl substituted propenoic acid (APP) copolymer derivatives. Furthermore, the present disclosure relates to methods of photostabilizing photoactive compositions comprising an APP copolymer derivative.

BACKGROUND OF THE DISCLOSURE

Increased public awareness regarding the hazards associated with exposure of human skin to ultraviolet (UV) radiation has contributed to the increasing popularity of UV-absorbing or scattering compounds (sunscreens), both independently and as a component of cosmetic products. However, the effectiveness of sunscreen products is directly linked to the efficiency of photo absorption/scattering in the UV range of electromagnetic radiation, in particular, UV-B (280-320 nm) and UV-A (320-400 nm).

Amongst the most widely used combinations of UV-absorbing compounds marketed today is 4-tert-butyl-4-methoxy-dibenzoylmethane (BMDBM) and octyl methoxycinnamate (OMC). Dibenzoylmethane derivatives, including BMDBM, are commonly selected as sunscreen components based on their ability to absorb the full spectrum of UV-A radiation (320-400 nm). Similarly, OMC is known for effectively absorbing electromagnetic radiation in the UV-B range (280-320 nm). However, neither compound alone or in combination is ideal due to their known photoinstability.

Exposure of a dibenzoylmethane derivative to UV-A radiation causes the excitation of an electron in the dibenzoylmethane derivative molecule from an initially occupied, lower energy orbital to a higher energy, previously unoccupied orbital. See Turro, Modern Molecular Photochemistry, 1991. In the electronically excited state, the dibenzoylmethane derivative is prone to degrade via the number of known pathways producing non-UVA-absorbing species and, therefore, can absorb little or no additional UVA energy. Similarly, exposure of OMC to UV radiation transforms the compound into a less absorbing cis-isomer, and thereby less effective at rendering UV absorption. Furthermore, when a dibenzoylmethane derivative (e.g., BMDBM) and OMC are exposed together to UV radiation, a photo reaction, known as the de Mayo reaction, occurs between the species resulting in the rapid disappearance of both species and, consequently, a loss of photoprotective effect.

To photostabilize an electronically excited UV-absorbing organic molecule (e.g., BMDBM), it must be returned to the ground state before it can undergo a photochemical reaction that is destructive to its UV radiation absorbing capabilities.

SUMMARY

Consequently, a need exists for an effective and safe light absorbing composition that is photochemically stable. Furthermore, a need exists for a composition capable of effectively photostabilizing photoactive compounds comprising dibenzoylmethane derivatives (e.g., BMDBM), OMC, and combinations thereof.

The present disclosure relates, in some embodiments, to photostable photoactive compositions comprising (a) at least one photoactive compound that develops within itself an excited state energy when subjected to UV radiation, and (b) a block copolymer comprising a plurality of blocks, and may have a structure according to Formula 1:

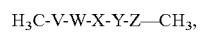

wherein the plurality of blocks comprises at least one block having a structure according to Formula II:

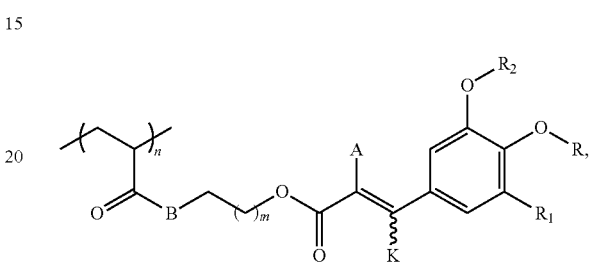

wherein R is $C_1$-$C_{30}$ alkyl; $R_1$ is selected from a group consisting of H, OH, and $C_1$-$C_{15}$ alkoxyl; $R_2$ is selected from a group consisting of H and $C_1$-$C_{15}$ alkyl; K is C1-C15 alkyl; B is selected from a group consisting of O and S; A is selected from a group consisting of CN and (C=O)$NR_3$($R_4$); and each stereoisomer is selected from a group consisting of E, Z, R, S, and a combination thereof, wherein the block copolymer is operable to quench the excited state energy. According to some embodiments, $R_3$ and $R_4$ are independently $C_1$-$C_{15}$ alkyl; wherein n is a number from 1 to 5,000; wherein m is a number from 0 to 20; and wherein R, $R_1$, $R_2$, $R_3$, and $R_4$ may be either straight chain or branched chain. According to some embodiments, at least one block may have a structure according to Formula III:

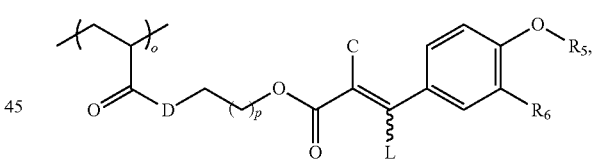

wherein $R_5$ is $C_1$-$C_{30}$ alkyl; $R_6$ is selected from a group consisting of H and $C_1$-$C_{15}$ alkyl; L is $C_1$-$C_{15}$ alkyl; D is selected from a group consisting of O and S; C is selected from a group consisting of CN and (C=O)$NR_7$($R_8$); and each stereoisomer is selected from a group consisting of E, Z, R, S, and a combination thereof; wherein $R_7$ and $R_8$ are independently $C_1$-$C_{15}$ alkyl; wherein o is a number from 1 to 5,000; wherein p is a number from 0 to 20; and wherein $R_5$, $R_6$, $R_7$ and $R_8$ may be either straight chain or branched chain. According to some embodiments, at least one block may have a structure according to Formula IV:

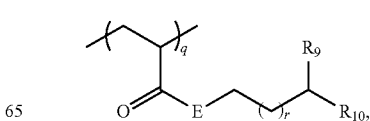

wherein $R_9$ and $R_{10}$ are independently $C_1$-$C_{15}$ alkyl, and E is selected from a group consisting of O and S; wherein q is a number from 1 to 5,000; and wherein r is a number from 0 to 20. According to some embodiments, at least one block may have a structure according to Formula V:

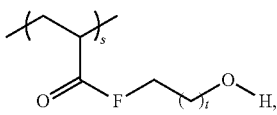

wherein F is selected from a group consisting of O and S; wherein s is a number from 1 to 5,000; and wherein t is a number from 0 to 20. In some embodiments, at least one block may have a structure according to Formula VI:

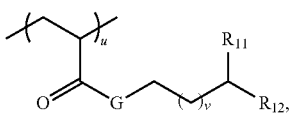

wherein $R_{11}$ and $R_{12}$ are independently $C_1$-$C_{15}$ alkyl, and G is selected from a group consisting of O and S; wherein u is a number from 1 to 5,000; and wherein v is a number from 0 to 20. In some embodiments, $R_9$=$R_{10}$, or $R_{11}$=$R_{12}$, but not both.

According to some embodiments, a block copolymer may be present at a concentration of from about 1% by weight to about 20% by weight, based on a total weight of a composition. For example, a block copolymer may be present at a concentration of from about 0.000001% by weight to about 20% by weight, based on a total weight of a composition. A block copolymer may be present at a concentration comprising about 15% by weight, about 10% by weight, about 5% by weight, about 1% by weight, about 0.000001% by weight, and a combination thereof, based on a total weight of a composition.

According to some embodiments, the present disclosure relates to photostable photoactive compositions, wherein at least one photoactive compound comprises 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof, menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof; coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bis-benzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

The present disclosure relates, in some embodiments, to photostable photoactive compositions, wherein at least one photoactive compound may be present at a concentration of from about 1% by weight to about 20% by weight, based on a total weight of a composition. In some embodiments, at least one photoactive compound may be present at a concentration comprising about 15% by weight, about 10% by weight, about 5% by weight, about 1% by weight, or a combination thereof, based on a total weight of a composition. A composition may include an oil phase having a dielectric constant of at least about 8. A composition may include an oil phase having a dielectric constant of at least about 7.

In some embodiments, a composition may enhance protection of at least one polymer against UV radiation, the at least one polymer comprising polyvinyl chloride, polystyrene, low-density polyethylene, high-density polyethylene, polyamides, nylon, polypropylene, rubber, and cellulose. According to some embodiments, a composition may enhance protection of at least one coating against UV radiation, the at least one coating comprising adhesives, acrylic paint, latex paint, stains, caulk, sealants, urethanes, enamels, films, and inks. A composition may enhance protection of a sunscreen against UV radiation, wherein application of a sunscreen to a skin of an animal (e.g., human) may protect a skin against UV radiation. In some embodiments, application of a coating to a surface (e.g., polymer, metal, canvas, or wood) may protect the surface against UV radiation.

The present disclosure relates, in some embodiments, to methods of photostabilizing photoactive compositions containing a block copolymer and at least one photoactive compound, the method comprising (a) adding at least one photoactive compound that develops within itself an excited state energy when subjected to UV radiation; and (b) adding the block copolymer in an effective amount to the composition, wherein the block copolymer is operable to quench the excited state energy; and wherein the photoactive composition protects a substrate from oxidative stress caused by absorption of light having a wavelength in the wavelength range from about 280 nm to about 400 nm. According to some embodiments, a block copolymer may comprise a plurality of blocks, and has a structure according to Formula I:

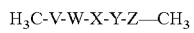

wherein the plurality of blocks comprises at least one block having a structure according to Formula II:

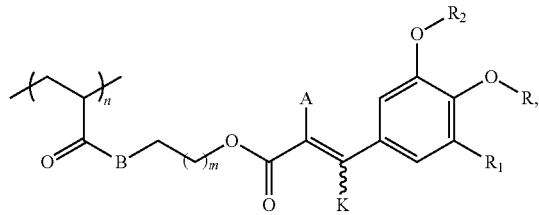

wherein R is $C_1$-$C_{30}$ alkyl; $R_1$ is selected from a group consisting of H, OH, and $C_1$-$C_{15}$ alkoxyl; $R_2$ is selected from a group consisting of H and $C_1$-$C_{15}$ alkyl; K is C1-C15 alkyl; B is selected from a group consisting of O and S; A is selected from a group consisting of CN and (C=O)$NR_3$($R_4$); and each stereoisomer is selected from a group consisting of E, Z, R, S, and a combination thereof, wherein the block copolymer is operable to quench the excited state energy. According to some embodiments, $R_3$ and $R_4$ are independently $C_1$-$C_{15}$ alkyl; wherein n is a number from 1 to 5,000; wherein m is a number from 0 to 20; and wherein R, $R_1$, $R_2$, $R_3$, and $R_4$ may be either straight chain or branched chain. According to some embodiments, at least one block may have a structure according to Formula III:

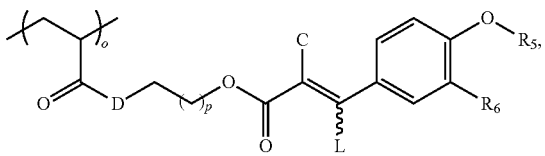

wherein $R_5$ is $C_1$-$C_{30}$ alkyl; $R_6$ is selected from a group consisting of H and $C_1$-$C_{15}$ alkyl; L is $C_1$-$C_{15}$ alkyl; D is selected from a group consisting of O and S; C is selected from a group consisting of CN and (C=O)$NR_7$($R_8$); and each stereoisomer is selected from a group consisting of E, Z, R, S, and a combination thereof; wherein $R_7$ and $R_8$ are independently $C_1$-$C_{15}$ alkyl; wherein o is a number from 1 to 5,000; wherein p is a number from 0 to 20; and wherein $R_5$, $R_6$, $R_7$ and $R_8$ may be either straight chain or branched chain. According to some embodiments, at least one block may have a structure according to Formula IV:

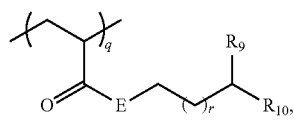

wherein $R_9$ and $R_{10}$ are independently $C_1$-$C_{15}$ alkyl, and E is selected from a group consisting of O and S; wherein q is a number from 1 to 5,000; and wherein r is a number from 0 to 20. According to some embodiments, at least one block may have a structure according to Formula V:

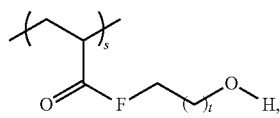

wherein F is selected from a group consisting of O and S; wherein s is a number from 1 to 5,000; and wherein t is a number from 0 to 20. In some embodiments, at least one block may have a structure according to Formula VI:

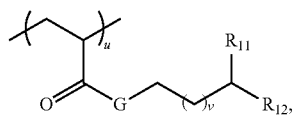

wherein $R_{11}$ and $R_{12}$ are independently $C_1$-$C_{15}$ alkyl, and G is selected from a group consisting of O and S; wherein u is a number from 1 to 5,000; and wherein v is a number from 0 to 20. In some embodiments, $R_9$=$R_{10}$, or $R_{11}$=$R_{12}$, but not both.

In some embodiments, the present disclosure relates to methods of photostabilizing photoactive compositions containing a block copolymer and at least one photoactive compound, wherein a substrate comprises a sunscreen, a cosmetic, a polymer, and a coating. In some embodiments, application of a sunscreen to a skin of an animal (e.g., human) may protect the skin against UV radiation. A polymer may comprise high-density polyethylene, low-density polyethylene, polystyrene, polyamides, nylon, polypropylene, rubber, cellulose, polyvinyl chloride, and polyvinyl alcohol. According to some embodiments, a coating may comprise stains, caulk, sealants, urethanes, enamels, films, adhesives, acrylic paints, latex paints, and inks. In some embodiments, a block copolymer may be present at a concentration from about 1% by weight to about 20% by weight, based on a total weight of a composition. For example, a block copolymer may be present at a concentration from about 0.000001% by weight to about 20% by weight, base on a total weight of a composition. In some embodiments, a block copolymer is present at a concentration comprising about 15% by weight, about 10% by weight, about 5% by weight, about 1% by weight, or a combination thereof, based on a total weight of a composition.

According to some embodiments, the present disclosure relates to methods of photostabilizing photoactive compositions containing a block copolymer and at least one photoactive compound, wherein the at least one photoactive compound comprises 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof; menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxy-cinnamic acid, its salts, and derivatives thereof; 1, 3, 5-triazine derivatives; methylene bis-benzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

In some embodiments, the present disclosure relates to methods of photostabilizing photoactive compositions containing a block copolymer and at least one photoactive compound, wherein the at least one photoactive compound may be present at a concentration of from about 0.000001% by weight to about 20% by weight, based on a total weight of a composition. In some embodiments, at least one photoactive compound may be present at a concentration comprising about 15% by weight, about 10% by weight, about 5% by weight, about 1% by weight, about 0.5% by weight, about 0.1% by weight, or a combination thereof, based on a total weight of a composition. A photoactive composition may include an oil phase having a dielectric constant of at least about 7. A photoactive composition may include an oil phase having a dielectric constant of at least about 8. In some embodiments, application of a cosmetic to a skin or a hair of an animal (e.g., human) thereby may protect the skin or the hair against UV radiation. Application of a sunscreen comprising a photoactive composition to a skin of an animal (e.g., human) may protect the skin against UV radiation.

The present disclosure, in some embodiments, relates to cosmetic or dermatological compositions for coating a skin to protect the skin from oxidative stress caused by adsorption of light having a wavelength in the wavelength range of about 280 nm to about 400 nm, the composition comprising (a) at least one photoactive compound that develops within itself an excited state energy when subjected to UV radiation and (b) a block copolymer comprising a plurality of blocks, having a structure according to Formula I:

H$_3$C-V-W-X-Y-Z—CH$_3$ wherein the block copolymer is operable to quench the excited state energy, and wherein the plurality of blocks comprises at least one block having a structure according to Formula II:

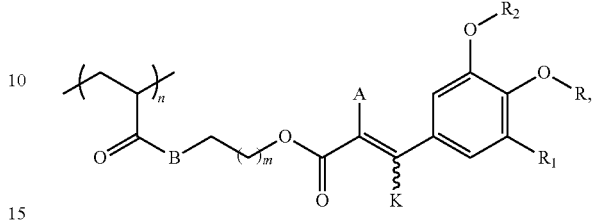

wherein R is $C_1$-$C_{30}$ alkyl; $R_1$ is selected from a group consisting of H, OH, and $C_1$-$C_{15}$ alkoxyl; $R_2$ is selected from a group consisting of H and $C_1$-$C_{15}$ alkyl; K is $C_1$-$C_{15}$ alkyl; B is selected from a group consisting of O and S; A is selected from a group consisting of CN and (C=O)NR$_3$(R$_4$); and each stereoisomer is selected from a group consisting of E, Z, R, S, and a combination thereof, wherein the block copolymer. According to some embodiments, $R_3$ and $R_4$ are independently $C_1$-$C_{15}$ alkyl; wherein n is a number from 1 to 5,000; wherein m is a number from 0 to 20; and wherein R, $R_1$, $R_2$, $R_3$, and $R_4$ may be either straight chain or branched chain. According to some embodiments, at least one block may have a structure according to Formula III:

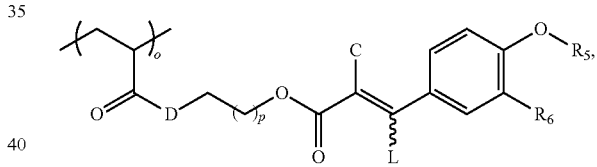

wherein $R_5$ is $C_1$-$C_{30}$ alkyl; $R_6$ is selected from a group consisting of H and $C_1$-$C_{15}$ alkyl; L is $C_1$-$C_{15}$ alkyl; D is selected from a group consisting of O and S; C is selected from a group consisting of CN and (C=O)NR$_7$(R$_8$); and each stereoisomer is selected from a group consisting of E, Z, R, S, and a combination thereof; wherein $R_7$ and $R_8$ are independently $C_1$-$C_{15}$ alkyl; wherein o is a number from 1 to 5,000; wherein p is a number from 0 to 20; and wherein $R_5$, $R_6$, $R_7$ and $R_8$ may be either straight chain or branched chain. According to some embodiments, at least one block may have a structure according to Formula IV:

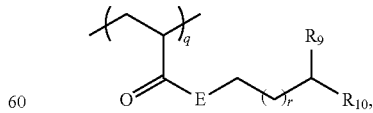

wherein $R_9$ and $R_{10}$ are independently $C_1$-$C_{15}$ alkyl, and E is selected from a group consisting of O and S; wherein q is a number from 1 to 5,000; and wherein r is a number from 0 to 20. According to some embodiments, at least one block may have a structure according to Formula V:

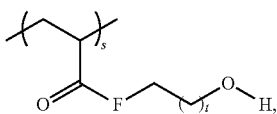

wherein F is selected from a group consisting of O and S; wherein s is a number from 1 to 5,000; and wherein t is a number from 0 to 20. In some embodiments, at least one block may have a structure according to Formula VI:

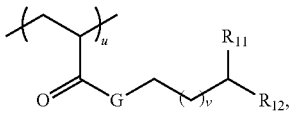

wherein $R_{11}$ and $R_{12}$ are independently $C_1$-$C_{15}$ alkyl, and G is selected from a group consisting of O and S; wherein u is a number from 1 to 5,000; and wherein v is a number from 0 to 20. In some embodiments, $R_9$=$R_{10}$, or $R_{11}$=$R_{12}$, but not both.

According to some embodiments, the present disclosure relates to cosmetic or dermatological compositions for coating a skin to protect the skin from oxidative stress caused by adsorption of light having a wavelength in the wavelength range of about 280 nm to about 400 nm, wherein a skin surface comprises human skin and animal skin. In some embodiments, a block copolymer is present at a concentration of about 1% to about 20% by weight, based on a total weight of a composition. A block copolymer may be present at a concentration comprising about 15% by weight, about 10% by weight, about 5% by weight, about 1% by weight, about 0.000001% by weight, or a combination thereof, based on a total weight of a composition.

In some embodiments, the present disclosure relates to cosmetic or dermatological compositions for coating a skin to protect the skin from oxidative stress caused by adsorption of light having a wavelength in the wavelength range of about 280 nm to about 400 nm, wherein the at least one photoactive compound comprises 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof, menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bis-benzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

In some embodiments, the present disclosure relates to cosmetic or dermatological compositions for coating a skin to protect the skin from oxidative stress caused by adsorption of light having a wavelength in the wavelength range of about 280 nm to about 400 nm, wherein at least one photoactive compound may be present at a concentration of about 0.000001% by weight to about 20% by weight, based on a total weight of a composition. According to some embodiments, at least one photoactive compound may be present at a concentration comprising about 15% by weight, about 10% by weight, about 5% by weight, about 1% by weight, about 0.5% by weight, about 0.1% by weight, or a combination thereof, based on a total weight of a composition. In some embodiments, a composition may include an oil phase having a dielectric constant of at least about 8. According to some embodiments, a composition may include an oil phase having a dielectric constant of at least about 7.

According to some embodiments, a block copolymer may be present at a concentration from about 1% by weight to about 20% by weight, based on a total weight of the composition. A block copolymer may be present at a concentration comprising about 15% by weight, about 10% by weight, about 5% by weight, about 1% by weight, or a combination thereof, based on the total weight of the composition. At least one photoactive compound may be present at a concentration from about 0.000001% by weight to about 20% by weight, based on the total weight of the composition. At least one photoactive compound is present at a concentration comprising about 15% by weight, about 10% by weight, about 5% by weight, about 1% by weight, about 0.5% by weight, about 0.1% by weight, or a combination thereof, based on the total weight of the composition. A photostable photoactive composition may include an oil phase having a dielectric constant of at least about 7. A photostable photoactive composition may include an oil phase having a dielectric constant of at least about 8. A photostable photoactive composition may enhance protection of at least one polymer against UV radiation, the at least one polymer comprising polyvinyl chloride, polystyrene, low-density polyethylene, high-density polyethylene, polyamides, nylon, polypropylene, rubber, and cellulose.

At least one photoactive compound may comprise 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butyl-phenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof, menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bis-benzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

According to some embodiments, a photostable photoactive composition may enhance protection of at least one coating against UV radiation, the at least one coating comprising adhesives, acrylic paint, latex paint, stains, caulk, sealants, urethanes, enamels, films, and inks. A photostable photoactive composition may enhance protection of a sunscreen against UV radiation, wherein application of said sunscreen to a skin of an animal may protect the skin against UV radiation. A photostable photoactive composition may enhance protection of a cosmetic against UV radiation, wherein application of said cosmetic to a skin or a hair of an animal may protect the skin or the hair against UV radiation. Application of a coating to a surface may protect the surface against UV radiation. A substrate may comprise a sunscreen, a cosmetic, a polymer, and a coating. Application of a sunscreen to a skin of an animal (e.g., human) may protect a skin against UV radiation. A polymer may comprise high-density polyethylene, low-density polyethylene, polystyrene, polyamides, nylon, polypropylene, rubber, cellulose, polyvinyl chloride, and polyvinyl alcohol. A coating may comprise stains, caulk, sealants, urethanes, enamels, films, adhesives, acrylic paints, latex paints, and inks. Application of a cosmetic to a skin or a hair of an animal (e.g., human) may protect the skin or hair against UV radiation. Application of a sunscreen to a skin of an animal (e.g., human) may protect the skin against UV radiation. A skin surface comprises human skin and animal skin.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein.

DETAILED DESCRIPTION

Figure 1:
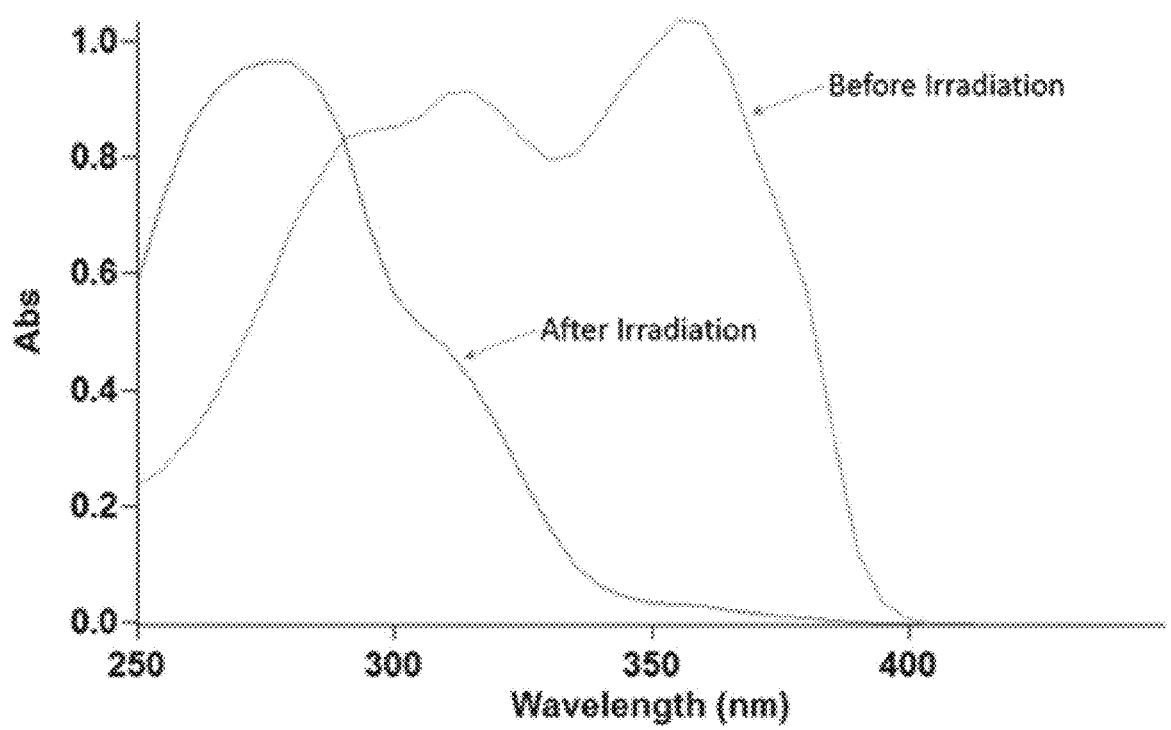
FIG. 1 is a graph illustrating the significant change in the UV radiation absorption spectra and decrease in UVA radiation absorption when a composition comprising BMDBM and OMC according to an embodiment of the disclosure were irradiated with UV light.

The present disclosure relates, in some embodiments, to para-alkoxyl phenyl substituted propenoic acid (APP) block copolymer derivatives capable of resolving excited energy states of certain photo unstable chromophores. Particularly, APP block copolymer derivatives may accept energy from electronically excited UV-radiation absorbing chromophore molecules, such as dibenzoylmethane derivatives, such that an excited state of these UV-radiation absorbing molecules is photostabilized (i.e., returned to a ground state). Upon photostabilization, a UV-radiation absorbing chromophore molecule is preserved and may be capable of absorbing additional UV radiation. Accordingly, enhanced protection of surfaces from UV radiation may be achieved by applying compositions comprising an APP block copolymer together with UV-absorbing materials (e.g., dibenzoylmethane derivatives). In some embodiments, a cosmetic, a sunscreen, a polymer (e.g., polyethylene), and/or a coating (e.g., paints) may comprise at least one APP block copolymer and at least one UV-absorbing compound, wherein applying the cosmetic, sunscreen, polymer, and/or coating to a surface (e.g., skin, hair, metal, polymer, plastic, canvas, or wood) may protect the applied surface from UV radiation.

This disclosure relates to sunscreen, cosmetic, polymer, coating, and dermatological compositions comprising a mixture of at least one photoactive compound (e.g., BMDBM) that develops within itself an excited state energy when subjected to UV radiation and at least one APP block copolymer, wherein the APP block copolymer is operable to quench the excited state energy from an excited state energy acceptor. This disclosure further relates to methods of photostabilizing a photoactive composition containing at least one photoactive compound and at least one block copolymer that may function as an excited state energy acceptor. In some embodiments, a method comprises (a) adding the at least one photoactive compound in an effective amount to a composition, wherein the at least one photoactive compound develops within itself an excited state energy when subjected to UV radiation; and (b) adding the block copolymer in an effective amount to the composition, wherein the block copolymer comprises a plurality of blocks.

The present disclosure relates to photostable photoactive compositions and methods of photostabilizing a photoactive composition. Compositions may comprise one or more photoactive compounds that may develop an excited state when subjected to UV radiation. Photostable photoactive compositions may also comprise an excited state energy acceptor comprising an APP block copolymers comprising a plurality of blocks, and having a structure according to Formula I:

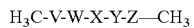

According to this disclosure APP block copolymers of Formula I are capable of photostabilizing photoactive compositions by operating as excited state energy acceptors/quenchers. However, this disclosure is not limited to any particular mechanism by which APP block copolymers of Formula I are capable of photostabilizing photoactive compositions.

In some embodiments an APP block copolymers may comprise a plurality of blocks, wherein the plurality of blocks may comprise at least one block having a structure according to Formula II:

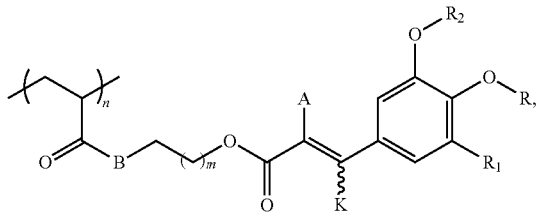

wherein R is $C_1$-$C_{30}$ alkyl; $R_1$ is selected from a group consisting of H, OH, and $C_1$-$C_{15}$ alkoxyl; $R_2$ is selected from a group consisting of H and $C_1$-$C_{15}$ alkyl; K is $C_1$-$C_{15}$ alkyl; B is selected from a group consisting of O and S; A is selected from a group consisting of CN and (C=O)NR$_3$(R$_4$); and each stereoisomer is selected from a group consisting of E, Z, R, S, and a combination thereof, wherein the block copolymer is operable to quench the excited state energy. Such substituent selections may provide a greater ability of a compound to accept energy and/or have an excited state with a shorter lifetime. According to some embodiments, $R_3$ and $R_4$ may be independently $C_1$-$C_{15}$ alkyl; wherein n is a number from 1 to 5,000; wherein m is a number from 0 to 20; and wherein R, $R_1$, $R_2$, $R_3$, and $R_4$ may be either straight chain or branched chain. According to some embodiments, at least one block may have a structure according to Formula III:

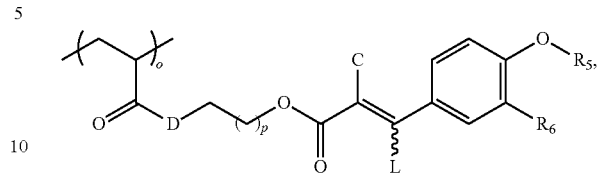

wherein $R_5$ is $C_1$-$C_{30}$ alkyl; $R_6$ is selected from a group consisting of H and $C_1$-$C_{15}$ alkyl; L is $C_1$-$C_{15}$ alkyl; D is selected from a group consisting of O and S; C is selected from a group consisting of CN and (C=O)NR$_7$(R$_8$); and each stereoisomer is selected from a group consisting of E, Z, R, S, and a combination thereof; wherein $R_7$ and $R_8$ are independently $C_1$-$C_{15}$ alkyl; wherein o is a number from 1 to 5,000; wherein p is a number from 0 to 20; and wherein $R_5$, $R_6$, $R_7$ and $R_8$ may be either straight chain or branched chain. Without being limited to any particular chemical mechanism of action, hydration of a phenolic hydroxyl group when R and/or $R_5$ is a hydrogen may lead to an extended lifetime of an excited state. Such extended excited state may result in formation of radicals and potential phototoxicity and/or photodegradation. Further, an alkoxyl substitution at a para position may be critical and may allow for a shorter lifetime of an electronically excited states of molecules. According to some embodiments, at least one block may have a structure according to Formula IV:

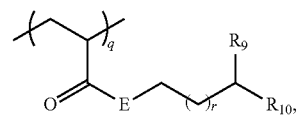

wherein $R_9$ and $R_{10}$ are independently $C_1$-$C_{15}$ alkyl, and E is selected from a group consisting of O and S; wherein q is a number from 1 to 5,000; and wherein r is a number from 0 to 20. According to some embodiments, at least one block may have a structure according to Formula V:

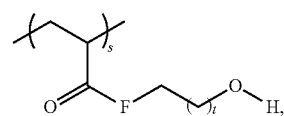

wherein F is selected from a group consisting of O and S; wherein s is a number from 1 to 5,000; and wherein t is a number from 0 to 20. In some embodiments, a photostable photoactive composition may have at least one block having a structure according to Formula VI:

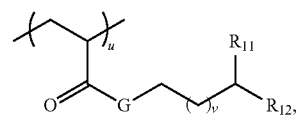

wherein $R_{11}$ and $R_{12}$ are independently $C_1$-$C_{15}$ alkyl, and G is selected from a group consisting of O and S; wherein u is a number from 1 to 5,000; and wherein v is a number from 0 to 20. In some embodiments, $R_9=R_{10}$, or $R_{11}=R_{12}$, but not both.

The present disclosure relates to photostable photoactive compositions and methods of photostabilizing a photoactive composition. Such compositions may comprise one or more photoactive compounds that develop an excited state when subjected to UV radiation. Photostabilized photoactive compositions may also comprise an excited state energy acceptor comprising one or more APP derivatives of Formula VII. According to this disclosure, APP derivatives of Formula VII are capable of photostabilizing photoactive compositions by serving as excited state energy acceptors. However, this disclosure is not limited to any particular mechanism by which APP derivatives of Formula VII are capable of photostabilizing photoactive compositions.

In some embodiments an APP analogue may comprise a structure according to Formula VII:

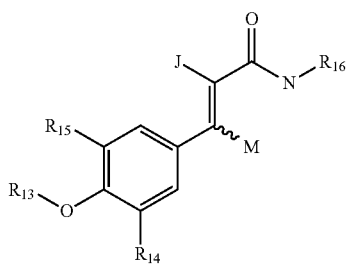

In some embodiments $R_{13}$ is selected from a group consisting of $C_1$-$C_{30}$ alkyl (straight chain or branched chain). For example, $R_{13}$ may comprise a methyl, ethyl, isopropyl, n-butyl, sec-butyl, or tert-butyl group. In some embodiments, $R_{13}$ is a hydrogen. Without being limited to any particular chemical mechanism of action, hydration of a phenolic hydroxyl group when $R_{13}$ is a hydrogen may lead to an extended lifetime of an excited state. Such extended excited state may result in formation of radicals and potential phototoxicity and/or photodegradation. Further, an alkoxyl substitution at a para position may be critical and may allow for a shorter lifetime of the electronically excited states of these molecules.

According to some embodiments, $R_{14}$ is selected from a group consisting of $C_1$-$C_{15}$ alkoxyl (straight chain or branched chain), OH, or H. For example, $R_{14}$ may include, but is not limited to methoxyl, ethoxyl, OH, or H. In some embodiments, $R_{15}$ is selected from a group consisting of H or $C_1$-$C_{15}$ alkoxyl (straight chain or branched chain). For example, $R_{15}$ may include, but is not limited to methoxyl, ethoxyl, OH, or H. In some embodiments $R_{16}$ is selected from a group consisting of $C_1$-$C_{40}$ alkyl (straight chain or branched chain). For example, $R_{16}$ may include, but is not limited to methyl, ethyl, propyl, butyl, pentyl, hexyl, or octyl. In some embodiments, the APP derivatives of Formula I comprise the Z stereoisomer, the E stereoisomer, or combinations thereof.

In some embodiments N is selected from a group consisting of O or S. In some embodiments, M is selected from the group consisting of $C_1$-$C_{15}$ alkyl. Such selections may provide a greater ability by a compound to accept energy and/or have an excited state with a shorter lifetime.

In some embodiments, J may be selected from a group consisting of CN or (C=O)$NR_{17}(R_{18})$, wherein $R_{17}$ and $R_{18}$ are independently selected from $C_1$-$C_{15}$ alkyl (straight chain or branched chain). For example, $R_{17}$ and $R_{18}$ can include, but are not limited to methyl, ethyl, propyl, butyl. According to some embodiments of the disclosure, A does not include (C=O)O-alkyl. A material comprising a (C=O)O-alkyl substituent at A may be thermodynamically unstable under basic conditions.

According to some embodiments, the present disclosure relates to methods of photostabilizing a photoactive composition containing a block copolymer and at least one photoactive compound. In some embodiments, a method may comprise (a) adding at least one photoactive compound in an effective amount to the composition and (b) adding a block copolymer according to Formula I in an effective amount to the composition, wherein the block copolymer comprises a plurality of blocks. In some embodiments, methods may comprise a block copolymer that may be operable to quench an excited state energy and a photoactive composition may protect a substrate from oxidative stress caused by adsorption of light having a wavelength in the wavelength range from about 280 nm to about 400 nm.

The present disclosure, in some embodiments may comprise an APP block copolymer as described herein present at a concentration from about 0.000001% by weight to about 20% by weight, based on a total weight of a composition. In some embodiments, at least one photoactive compound may be present at a concentration of about 1% to about 20%, based on a total weight of a composition. In some embodiments, an APP block copolymer is present at a concentration comprising about 15% by weight, about 10% by weight, about 5% by weight, about 1% by weight, about 0.5% by weight, about 0.1% by weight, or a combination thereof, based on a total weight of a composition.

In some embodiments, a sunscreen, cosmetic, polymer, coating, or dermatological composition may comprise an APP block copolymer as described herein present at a concentration of about 0.000001% by weight to about 20% by weight, based on a total weight of a composition. In some embodiments, a concentration of an APP block copolymer is present at a concentration comprising about 15% by weight, about 10% by weight, about 5% by weight, about 1% by weight, about 0.5% by weight, about 0.1% by weight, or a combination thereof, based on a total weight of a composition.

The present disclosure relates, in some embodiments, to methods of photostabilizing a photoactive composition containing a block copolymer and at least one photoactive compound, wherein an APP block copolymer as described herein may be present at a concentration of about 0.000001% by weight to about 20% by weight, based on a total weight of a composition. In some embodiments, an APP block copolymer may be present at a concentration of about 1% by weight to about 20% by weight, based on a total weight of a composition. In some embodiments, an APP block copolymer may be present at a concentration comprising about 15% by weight, about 10% by weight, about 5% by weight, about 1% by weight, about 0.5% by weight, about 0.1% by weight, or a combination thereof, based on a total weight of a composition.

The present disclosure, in some embodiments, may comprise block copolymer derivatives of Formula I that may stabilize photoactive compounds that develop excited states when subjected to UV radiation. In some embodiments, photoactive compounds may include dibenzoyl methane derivatives such as: 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethyl dibenzoylmethane; 4,4'-diisopropyl dibenzoylmethane; 4,4'-dimethoxy dibenzoylmethane; 4-tert-butyl-4'-methoxy dibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; and 2,6-dimethyl-4-tert-butyl-4'-methoxydibenzoylmethane.

In some embodiments photoactive compounds may be alternatively described as UV-absorbing compounds and/or UV filtering compounds. UV-absorbing compounds may include octyl methoxycinnamate (OMC), octocrylene, salicylic acid esters (e.g., ethylhexyl salicylate and homomenthyl salicylate,), p-methoxycinnamic acid esters (e.g., ethylhexyl methoxycinnamate and isoamyl methoxycinnamate), avobenzone (also known as butyl methoxydibenzoylmethane), oxybenzone, bis-ethylhexyloxyphenol methoxyphenyl triazone, methylene bis-benzotriazolyl tetramethylbutylphenol, 4-methylbenzylidene camphor, diethylamino hydroxyl benzoyl hexyl benzoate, drometrizole trisiloxane, ethylhexyl triazone, diethylhexyl butamido triazone, terephthalylidene dicamphor sulfonic acid and its salts, and menthyl anthranilate.

In some embodiments, photoactive compounds that develop excited states when subjected to UV radiation may comprise p-aminobenzoic acid, its salts, and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, (+)-menthyl, (−)-menthyl, glyceryl, and dipropyleneglycol esters); cinnamic acid derivatives ((+)-menthyl, (−)-menthyl, and benzyl esters, alpha-phenyl cinnamonitrile; butyl cinnamoyl pyruvate); coumarin derivatives umbelliferone, methylumbelliferone, methylaceto-umbelliferone); camphor derivatives (3 benzylidene, 4-methylbenzylidene, polyacrylamidomethyl benzylidene, benzalkonium methylsulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinolone derivatives (8-hydroxyquinoline salts, 2-phenylquinoline); hydroxy- or methoxy-substituted benzophenones; uric acid derivatives; violuric acid derivatives; tannic acid and its derivatives; hydroquinone; benzophenones (oxybenzone, sulisobenzone, dioxybenzone, benzoresorcinol, octabenzone, 4-isopropyldibenzoylmethane, butyl methoxydibenzoylmethane, etocrylene, and 4-isopropyldibenzoylmethane); 2-ethylhexyl p-methoxycinnamate; 4,4'-t-butyl methoxydibenzoylmethane; octyldimethyl p-aminobenzoate; digalloyl trioleate; ethyl 4-[bis(hydroxypropyl)]aminobenzoate; 2-ethylhexyl salicylate; glycerol p-aminobenzoate; 3,3,5-trimethylcyclohexylsalicylate; and combinations thereof.

Photoactive compositions may include at least one UV-A radiation absorbing (320-400 nm) photoactive compound and at least one UV-B radiation absorbing (280-320 nm) photoactive compound. According to some embodiments, photoactive compounds that develop excited states when subjected to UV radiation may comprise 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof, menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives its, salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bis-benzotriazolyl tetramethylbutylphenol, it salts and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

According some embodiments, photoactive compounds that develop excited states when subjected to UV radiation may comprise aminobenzoic acid, cinoxate, dioxybenzone, homosalate, menthyl anthranilate, octocrylene, octyl methoxycinnamate, octyl salicylate, oxybenzone, padimate 0, phenylbenzimidazole sulfonic acid, sulisobenzone, titanium dioxide, trolamine salicylate; zinc oxide, diethanolamine methoxycinnamate, ethyl-[bis(hydroxypropyl)] aminobenzoate, glyceryl aminobenzoate, 4-isopropyl dibenzoylmethane, 4-methylbenzylidene camphor, terephthalylidene dicamphor sulfonic acid, sulisobenzone, camphor benzalkonium methosulfate, homosalate, benzophenone, terephthalydene dicamphor sulfonic acid, benzylidene camphor sulfonic acid, polyacrylamidomethyl benzylidene camphor, PEG-25 PABA, isoamyl p-methoxycinnamate, ethylhexyl triazone, drometrizole trisiloxane, diethylhexyl butamido triazone, 4-methylbenzylidene camphor, benzylidene camphor, ethylhexyl salicylate, ethylhexyl dimethyl PABA, methylene bis benztriazolyl tetramethylbutylphenol, disodium phenyl dibenzimidazole tetrasulfonate, bis ethylhexyloxyphenol methoxyphenol triazine, methylene bisbenzotriazolyl tetramethylbutylphenol, 4-(2-oxo-3-bornylidenemethyl)benzene-sulfonic acid, 2-methyl-5-(2-oxo-3-bornylidenemethyl)sulfonic acid and the salts thereof, 2-(4'-diethylamino-2'-hydroxybenzoyl) benzoic acid hexyl ester, 2,2'-methylenebis(6-(2H-benzotriazol-2-yl)-4-(1,1,3, 3-tetramethylbutyl)phenol), bisoctyltriazole, diethylhexyl 2,6-naphthalate, and bisethylhexyloxyphenol methoxyphenyl triazine.

A photoactive compound may be considered stable when, for example, after about a 30 Minimum Erythemal Dose ("MED") irradiation, the photoactive compound has retained at least about 90% of its original absorbance at a wavelength, or over a range of wavelengths of interest (e.g., a wavelength at which a photoactive compound has a peak absorbance, such as 350-370 nm for Avobenzone). In some embodiments, a sunscreen, a cosmetic, a polymer, a coating, or a dermatological composition may include a plurality of photoactive compounds and may be considered stable as a whole when, for example, after about a 30 MED irradiation, the sunscreen, cosmetic, or dermatological composition has retained at least about 90% of its original absorbance at one or more wavelengths of interest (e.g., at or near a peak absorbance wavelength of a primary photoactive compound). According to some embodiments, a composition comprising an effective amount of at least one APP derivative may include a concentration of at least one APP derivative, wherein after about a 30 MED irradiation, the composition retains at least about 90% of its original absorbance at one or more wavelengths of interest.

The present disclosure, in some embodiments may comprise at least one photoactive compound as described herein present at a concentration of about 0.000001% by weight to about 20% by weight, based on a total weight of a composition. In some embodiments, at least one photoactive compound may be present at a concentration of about 1% by weight to about 20% by weight, based on a total weight of a composition. In some embodiments, at least one photoactive compound may be present at a concentration comprising about 15% by weight, about 10% by weight, about 5% by weight, about 1% by weight, about 0.5% by weight, about 0.1% by weight, or a combination thereof, based on a total weight of a composition.

In some embodiments, a sunscreen, cosmetic, polymer, coating, or dermatological composition may comprise at least one photoactive compound as described herein present at a concentration of about 0.000001% by weight to about 20% by weight, based on a total weight of a composition. In some embodiments, a concentration of at least one photoactive compound may be present at a concentration comprising about 15% by weight, about 10% by weight, about 5% by weight, about 1% by weight, about 0.5% by weight, about 0.1% by weight, or a combination thereof, based on a total weight of a composition.

The present disclosure relates, in some embodiments, to methods of photostabilizing a photoactive composition containing a block copolymer and at least one photoactive compound, the methods comprising at least one photoactive compound as described herein present at a concentration of about 0.000001% by weight to about 20% by weight, based on a total weight of a composition. In some embodiments, at least one photoactive compound may be present at a concentration of about 1% by weight to about 20% by weight, based on a total weight of a composition. In some embodiments, at least one photoactive compound is present at a concentration comprising about 15% by weight, about 10% by weight, about 5% by weight, about 1% by weight, about 0.5% by weight, about 0.1% by weight, or a combination thereof, based on a total weight of a composition.

According to some embodiments, a photoactive composition may include one or more photoactive compounds, wherein the photoactive compound(s) may act to absorb UV radiation and thereby protect a substrate comprising a sunscreen, a cosmetic, a polymer, and a coating from effects of UV radiation. Further, application of a substrate comprising a photoactive composition to a surface comprising skin (e.g., animal or human), hair (e.g., animal or human), wood, metal, glass, and plastic, protects the surface from effects of UV radiation. In some embodiments, a polymer may comprise high-density polyethylenes, low-density polyethylenes, polytetrafluoroethenes, polyureas, polyamides, epoxy resins, polysaccharides, polyurethanes, polymethyl methacrylate, polystyrenes, polyamides, nylons, polypropylenes, rubbers, celluloses, polyvinyl chlorides, polyesters, polycarbonates, and polyvinyl alcohols. Coatings may comprise adhesives, acrylic paint, latex paint, stains, caulk, sealants, urethanes, enamels, films, and inks. Photostable photoactive compositions comprising an APP block copolymer may enhance protection of a sunscreen against UV radiation, wherein application of said sunscreen to a skin and/or a hair of an animal (e.g., human) may protect the skin and/or hair against UV radiation.

An absorption process may cause a photoactive compound to reach an excited state, wherein the excited state is characterized by the presence of excited electronic energy (e.g., singlet state energy or triplet state energy), as compared to a ground state of the photoactive compound. Once a photoactive compound reaches an excited state, there exists a number of pathways by which the excited photoactive compound can dissipate its excess energy (e.g., singlet and/or triplet energy), however, many of those pathways adversely affect the ability of the photoactive compound to further absorb UV radiation. For example, if the pathway results in a structural rearrangement of the photoactive compound (e.g., De Mayo reaction and fragmentation). APP block copolymer derivatives may accept electronic excited state energy from UV absorbers, providing photostability to photoactive compounds. In some embodiments, an acceptance of electronic excited state energy by an APP block copolymer from a photoactive compound may result in the photoactive compound returning to a ground state energy configuration or an at least partially lower energy state. In some embodiments, APP block copolymers may provide electronic excited state energy quenching of UV-radiation absorbing compounds in compositions, the compositions comprising sunscreen, cosmetic, polymer, coating, and dermatological formulations. Sunscreens, cosmetics, or dermatological compositions may be used for coating a skin surface to protect skin from UV radiation damage when exposed to sunlight, or other UV radiation. In some embodiments, sunscreen, cosmetic, or dermatological compositions include a UV-A radiation filter and/or a UV-B radiation filter compound and/or a broad-band filter compound, particularly a dibenzoylmethane derivative UV-A radiation filter that is photostabilized by at least one APP block copolymer for protection of skin from UV-A and/or UV-B wavelength radiation.

In some embodiments, APP block copolymers may be hydrophobic and may not be water soluble. Waterproof sunscreen, cosmetic, or dermatological compositions may comprise at least one hydrophobic APP block copolymer analogue. In some embodiments, compositions and methods may comprise an oil phase. An oil phase may further comprise at least one polar solvent, wherein at least one polar solvent may increase a polarity of an oil phase of a composition including APP block copolymer derivatives. In some embodiments, increasing a polarity of an oil phase of a composition may increase a photostability of photoactive compounds in a composition. In some embodiments, at least one polar solvent is present in an oil-phase of a composition, wherein the amount of polar solvent present may increase a dielectric constant of the oil-phase of the composition to a dielectric constant of at least about 7. Enough polar solvent may be present to raise a dielectric constant of an oil-phase of a composition to at least about 8. In some embodiments, polar solvents comprise acetone, ethanol, n-butanol, isopropanol, acetonitrile, ethyl acetate, dimethyl sulfoxide, water, and combinations thereof.

In some embodiments, sunscreen, cosmetic, or dermatological compositions described herein may comprise an APP block copolymer derivative and one or more photoactive compounds. Compositions may include both UV-A and UV-B radiation absorbing photoactive compounds in a cosmetically acceptable carrier, optionally including additives, such as emollients, stabilizers, emulsifiers, and combinations thereof. Additives may be used in preparing a sunscreen, cosmetic, or dermatological composition in an emulsion (oil-in-water or water-in-oil) from a composition that includes one or more photoactive compounds and a solvent or a solvent combination that includes one or more organic solvents and water. An emulsion may be an oil-in-water emulsion, wherein an oil phase is primarily formed from a mixture of a UV radiation filter compound(s), and may include a dibenzoylmethane derivative, such as Avobenzone, and one or more organic solvents.

In some embodiments, a composition comprising an APP block copolymer and at least one photoactive compound may be used for sunscreen, cosmetic, or dermatological compositions, wherein compositions treat, care, decorate, and/or cleanse skin and/or hair from an animal (e.g., human). Sunscreen, cosmetic, or dermatological compositions may comprise cosmetic auxiliaries such as those conventionally used in such preparations, such as preservatives, bactericides, perfumes, antifoaming agents, dyes, pigments which have a coloring effect, thickeners, moisturizers and/or humectants, fats, oils, waxes or other conventional constituents of a sunscreen, cosmetic, or dermatologic formulation, other conventional constituents comprising alcohols, polyols, polymers, foam stabilizers, electrolytes, organic solvents, silicone derivatives, or combinations thereof.

As will be understood by those skilled in the art who have the benefit of the instant disclosure, other equivalent or alternative compositions and methods for formulating a photostable UV radiation absorbing composition comprising APP block copolymer derivatives can be envisioned without departing from the description contained herein. Accordingly, the manner of carrying out the disclosure as shown and described is to be construed as illustrative only.

Persons skilled in the art may make various changes in the identity and quantity of components without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition of the disclosure. For example, a composition, device, and/or system may be prepared and or used as appropriate for animal and/or human use (e.g., with regard to sanitary, infectivity, safety, toxicity, biometric, and other considerations). Elements, compositions, devices, systems, methods, and method steps not recited may be included or excluded as desired or required.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

UV light exposure is often measured in MED rather than a measurement of time. MED relates to the minimal dosage of UV exposure required to result in redness 24 hours after exposure. Although technically an individualized measurement that would vary depending on the sensitivity of an individual's skin, MED measurements have been standardized with the advent of UV bulbs and lamps.

Example 1: Comparing the Photostability of a Composition Containing BMDBM and OMC FIG. 1 illustrates the photoinstability of a composition containing BMDBM and OMC. As shown in FIG. 1, a composition containing an acetonitrile solution including 10 ppm BMDBM and 10 ppm OMC was irradiated with 0 MED (before irradiation line) and 15 MED (after irradiation line) of UV light. Absorption was measured for wavelengths 250 nm to 500 nm in length. BMDBM absorbs wavelengths around 375 nm in length, which can be seen as a distinct peak on the line illustrating the composition which was not irradiated with UV light. However, as shown in FIG. 1, after 15 MED UV irradiation, the BMDBM peak at 375 nm is substantially diminished. Thus, FIG. 1 illustrates that the BMDBM in the composition had a drastically reduced capability of absorbing light after exposure to 15 MED UV irradiation.

Figure 2:
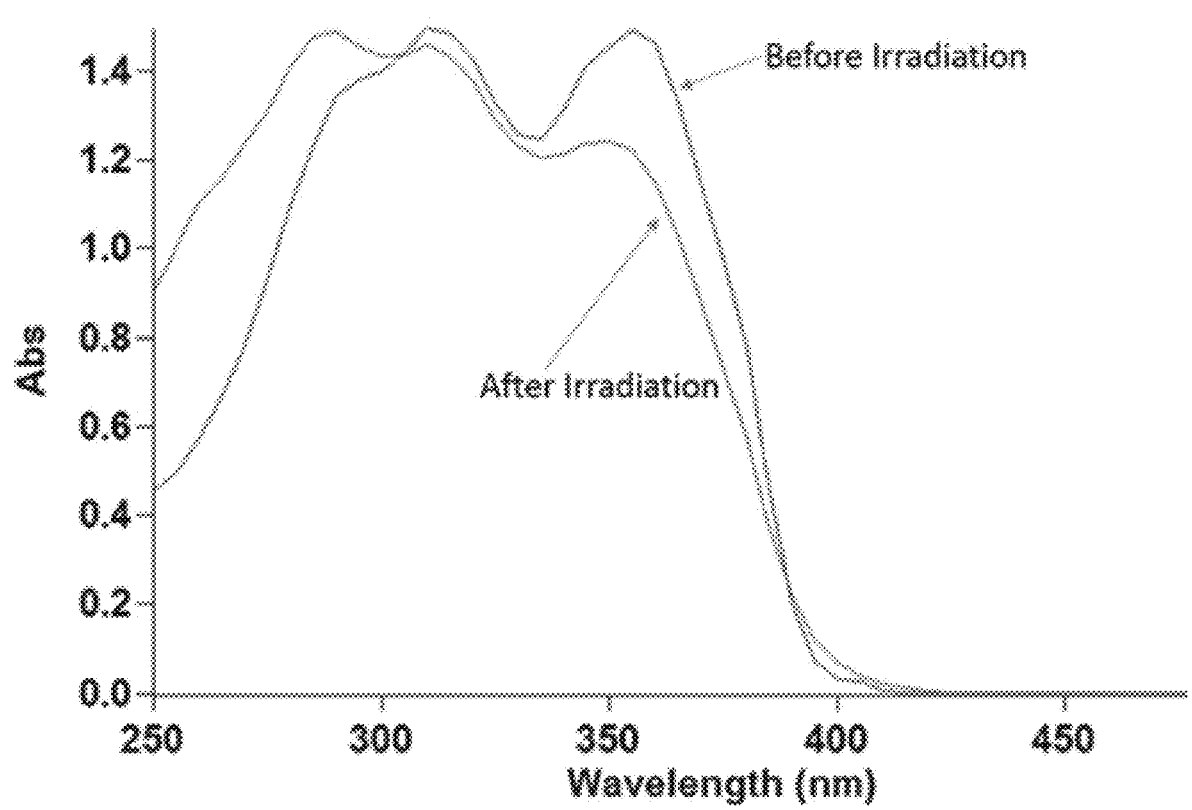
FIG. 2 is a graph illustrating the UV radiation absorption spectra when a composition comprising BMDBM, OMC, and APP according to an embodiment of the disclosure were irradiated with UV light.

Example 2: Photostabilization of a Photoactive Composition with an APP Analogue FIG. 2 illustrates the photostabilization of a photoactive composition by the addition of an APP analogue of Formula VII. As shown in FIG. 2, a composition containing an acetonitrile solution of 10 ppm BMDBM, 10 ppm of OMC, and 5 ppm of an APP analogue of Formula VII was irradiated with 0 MED (Before irradiation line) and 15 MED (After irradiation line) of UV light. As shown in FIG. 2, the BMDBM peak at 375 nm is only moderately diminished after exposure of the composition to 15 MED (blue line). Thus, FIG. 2 illustrates that the APP analogue of Formula VII had a photostabilizing effect on the composition.

Example 3: Comparing the Stability of Compositions with and without APP

Figure 3:
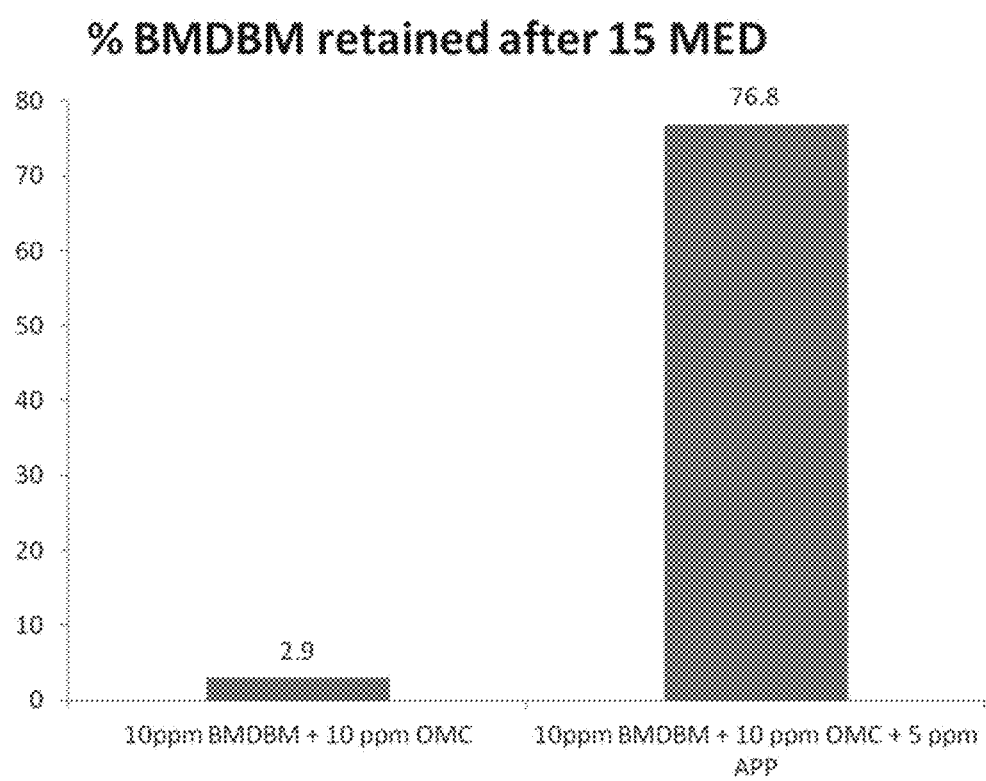
FIG. 3 is a graph illustrating the amount of BMDBM remaining in a composition according to an embodiment of the disclosure after irradiation with UV light.

FIG. 3 illustrates the percentage of BMDBM remaining in compositions after irradiation with 15 MED of UV light. As shown in FIG. 3, only 2.9% of the BMDBM of a composition containing 10 ppm BMDBM and 10 ppm OMC remained capable of absorbing light at 375 nm after being irradiated with 15 MED of UV light. By contrast, approximately 76.8% of the BMDBM of a composition containing 10 ppm BMDBM, 10 ppm OMC, and 5 ppm of an APP analogue of Formula VII retained the ability to absorb light at 375 nm. Thus, as illustrated in FIG. 3, APP derivatives of Formula VII are capable of photostabilizing photoactive compositions.

Example 4: Phosphorescence Measurement in Ethanol Glass at 77K

Figure 4:
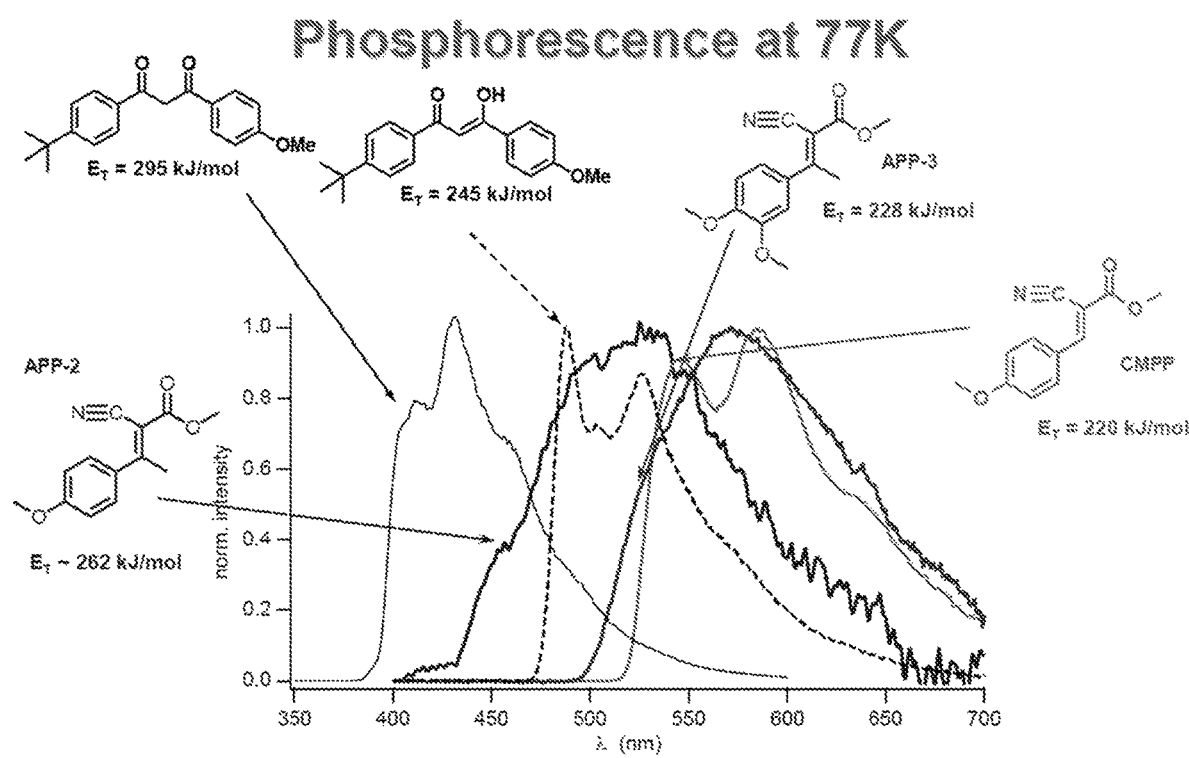
FIG. 4 is a graph illustrating the phosphorescence spectra of APP analogues and Avobenzone in ethanol glass at 77K.

Phosphorescence lifetimes were measured at 77 K exciting with pulses from a Lambda Physik dye laser (FL3002; Laser dye: Stilbene 3) which was pumped with a Lambda Physik Excimer laser (Lextra 50) (FIG. 4). The phosphorescence was collected and isolated using lenses and monochromators (H10 for Vis spectral range and 1681B for NIR spectral range; Jobin-Yvon Inc.) and focused onto Hamamatzu photomultiplier tubes (PMT) (R928 for the visible spectral range and H9170-45 for NIR spectral range). The photocurrent from the PMT was amplified (SR 560, Stanford Research Systems) and stored on a digital oscilloscope (TDS 360, Tektronix). We estimate the lifetime measurement error to be 5%. Phosphorescence spectra in ethanol glass at 77K. Methyl iodide (MEI) was added to increase the phosphorescence yields for APP-2 (33% MeI), APP-3 (20% MeI) and CMPP (20% MeI). The phosphorescence for APP-2 was very weak. APP-3 and CMPP are may quench triplet states of both, the keto and enol form of avobenzone by energy transfer. APP-2 may quench triplet states of the keto form as seen in FIG. 4.

Example 5: Ketone Triplet State Quenching by APP Derivatives

Figure 5:
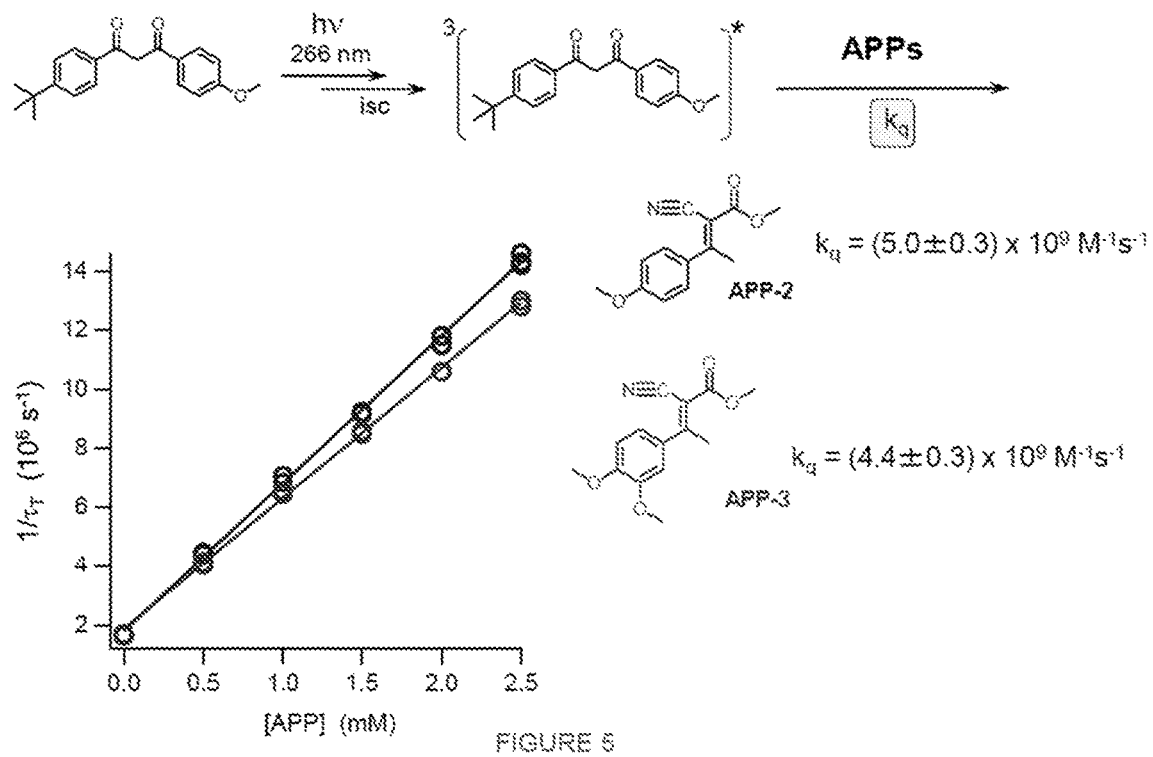
FIG. 5 is a graph illustrating ketone triplet state quenching by APP analogues as measured by a laser flash photolysis of a ketone in the presence of varying concentrations of APP analogues in deoxygenated acetonitrile solutions.
Figure 6:
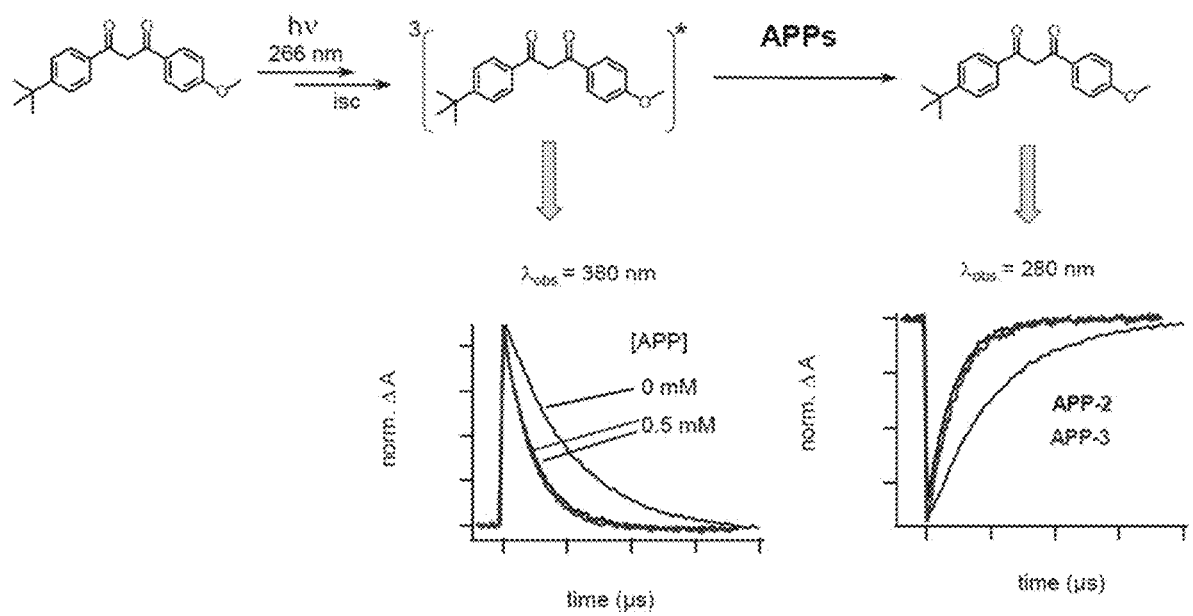
FIG. 6 is a set of graphs illustrating APP analogues quenching the ketone triplet state by recovering the ground state of the ketone.
Figure 7:
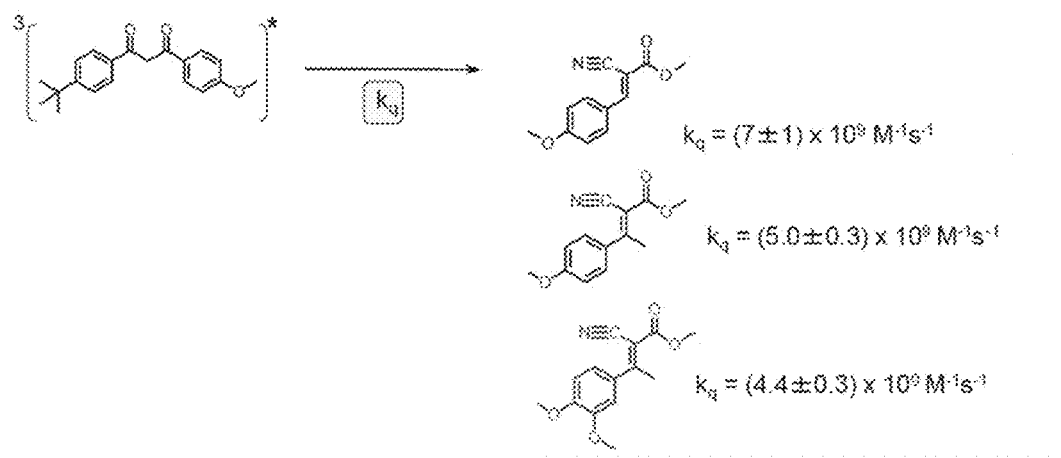
FIG. 7 illustrates the ketone triplet state quenching rate constants of various APP analogues.

The nanosecond flash photolysis system employs the a Quanta Ray DCR 2A Nd:YAG laser (third [=355 nm] harmonic, 8-nanoseconds at full width at half maximum (ns fwhm), typical laser energy=10-15 mJ/pulse at 20 Hz), and a Bruker broad band preamplifier with a response time of 60 ns for excitation. A pulsed Xenon lamp, combined with an ISA H10 monochromator, serves as the monitoring system (See FIGS. 5-7). Typically data acquired after 10-15 laser pulses were averaged to produce each experimental trace both in the kinetic experiments and in the acquisition of a transient absorption spectra. Quartz cells having cross sections of 1×1 cm were used. Laser flash photolysis of keto-avobenzone (266 nm, 5 ns pulse width) were carried out in deoxygenated acetonitrile solutions. To determine the quenching rate constant of triplet keto-avobenzone, decay traces of the triplet absorption of keto-avobenzone in the absence and presence of varying concentrations of APPs were recorded. Keto-avobenzone was generated by photolysis of enol-avobenzone at 350 nm.

What is claimed is:

1. A photostable photoactive composition comprising:
   (a) at least one photoactive compound that develops within itself an excited state energy when subjected to UV radiation, and
   (b) a block copolymer comprising a plurality of blocks, and
   having a structure according to Formula I:

$H_3C$-V-W-X-Y-Z—$CH_3$ wherein the plurality of blocks comprises:
   at least one block having a structure according to Formula II:

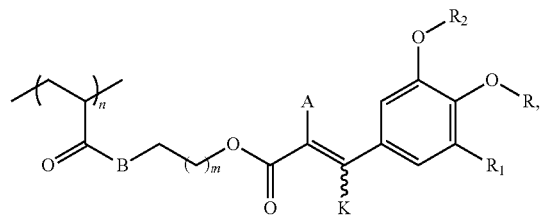

wherein:
   R is $C_1$-$C_{30}$ alkyl;
   $R_1$ is selected from the group consisting of H, OH, and $C_1$-$C_{15}$ alkoxyl;
   $R_2$ is selected from the group consisting of H and $C_1$-$C_{15}$ alkyl;
   K is $C_1$-$C_{15}$ alkyl;
   B is selected from the group consisting of O and S;
   A is selected from the group consisting of CN and (C=O)$NR_3(R_4)$; and
   each stereoisomer is selected from the group consisting of E, Z, R, S, and a combination thereof;
   wherein $R_3$ and $R_4$ are independently $C_1$-$C_{15}$ alkyl;
   wherein n is a number from 1 to 5,000;
   wherein m is a number from 0 to 20;
   wherein R, $R_1$, $R_2$, $R_3$, and $R_4$ may be either straight chain or branched chain;
   at least one block having a structure according to Formula III:

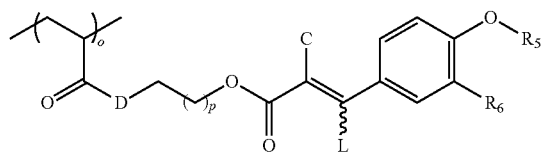

wherein:
R₅ is $C_1$-$C_{30}$ alkyl;
R₆ is selected from the group consisting of H and $C_1$-$C_{15}$ alkyl;
L is $C_1$-$C_{15}$ alkyl;
D is selected from the group consisting of O and S;
C is selected from the group consisting of CN and (C=O)NR₇(R₈); and
each stereoisomer is selected from the group consisting of E, Z, R, S, and a combination thereof;
wherein R₇ and R₈ are independently $C_1$-$C_{15}$ alkyl;
wherein o is a number from 1 to 5,000;
wherein p is a number from 0 to 20;
wherein R₅, R₆, R₇ and R₈ may be either straight chain or branched chain;
at least one block having a structure according to Formula IV:

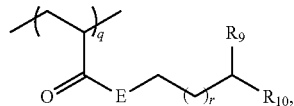

wherein:
R₉ and R₁₀ are independently $C_1$-$C_{15}$ alkyl, and
E is selected from the group consisting of O and S;
wherein q is a number from 1 to 5,000;
wherein r is a number from 0 to 20; and
at least one block having a structure according to Formula V:

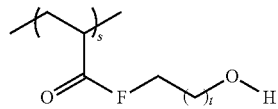

wherein:
F is selected from the group consisting of O and S;
wherein s is a number from 1 to 5,000;
wherein t is a number from 0 to 20;
wherein the block copolymer is operable to quench the excited state energy.

2. A photostable photoactive composition according to claim 1, wherein at least one block has a structure according to Formula VI:

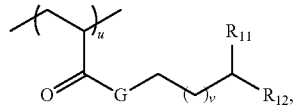

wherein:
R₁₁ and R₁₂ are independently $C_1$-$C_{15}$ alkyl, and
G is selected from the group consisting of O and S;
wherein u is a number from 1 to 5,000;
wherein v is a number from 0 to 20;
wherein R₉=R₁₀, or R₁₁=R₁₂, but not both.

3. A photostable photoactive composition according to claim 1, wherein the block copolymer is present at a concentration of about 1% by weight to about 20% by weight, based on a total weight of the composition.

4. A photostable photoactive composition according to claim 1, wherein the block copolymer is present at a concentration comprising about 15% by weight, about 10% by weight, about 5% by weight, about 1% by weight, or a combination thereof, based on the total weight of the composition.

5. A photostable photoactive composition according to claim 1, wherein the at least one photoactive compound comprises 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof, menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxynaphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bis-benzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

6. A photostable photoactive composition according to claim 1, wherein the at least one photoactive compound is present at a concentration of about 0.000001% by weight to about 20% by weight, based on the total weight of the composition.

7. A photostable photoactive composition according to claim 1, wherein the at least one photoactive compound is present at a concentration comprising about 15% by weight, about 10% by weight, about 5% by weight, about 1% by weight, about 0.5% by weight, about 0.1% by weight, or a combination thereof, based on the total weight of the composition.

8. A photostable photoactive composition according to claim 1, wherein said composition includes an oil phase having a dielectric constant of at least about 8.

9. A photostable photoactive composition according to claim 1, wherein said composition may enhance protection of at least one polymer against UV radiation, the at least one polymer comprising polyvinyl chloride, polystyrene, low-density polyethylene, high-density polyethylene, polyamides, nylon, polypropylene, rubber, and cellulose.

10. A photostable photoactive composition according to claim 1, wherein said composition may enhance protection of at least one coating against UV radiation, the at least one coating comprising adhesives, acrylic paint, latex paint, stains, caulk, sealants, urethanes, enamels, films, and inks.

11. A photostable photoactive composition according to claim 1, wherein said composition may enhance protection of a sunscreen against UV radiation, wherein application of said sunscreen to a skin of an animal may protect the skin against UV radiation.

12. A photostable photoactive composition according to claim 1, wherein said composition may enhance protection of a cosmetic against UV radiation, wherein application of said cosmetic to a skin or a hair of an animal may protect the skin or the hair against UV radiation.

13. A photostable photoactive composition according to claim 9, wherein application of said coating to a surface may protect the surface against UV radiation.

14. A method of photostabilizing a photoactive composition containing a block copolymer and at least one photoactive compound, the method comprising:
(a) adding the at least one photoactive compound in an effective amount to the composition,
   wherein the at one photoactive compounds develops within itself an excited state energy when subjected to UV radiation; and
(b) adding the block copolymer in an effective amount to the composition,
   wherein the block copolymer comprises a plurality of blocks, and has a structure according to Formula I:

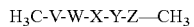

wherein the plurality of blocks comprises:
   at least one block having a structure according to Formula II:

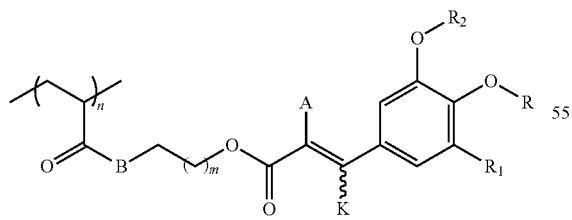

wherein:
R is $C_1$-$C_{30}$ alkyl;
$R_1$ is selected from the group consisting of H, OH, and $C_1$-$C_{15}$ alkoxyl;
$R_2$ is selected from the group consisting of H and $C_1$-$C_{15}$ alkyl;
K is $C_1$-$C_{15}$ alkyl;

B is selected from the group consisting of O and S;
A is selected from the group consisting of CN and (C=O)NR$_3$(R$_4$); and
each stereoisomer is selected from the group consisting of E, Z, R, S, and a combination thereof;
wherein $R_3$ and $R_4$ are independently $C_1$-$C_{15}$ alkyl;
wherein n is a number from 1 to 5,000;
wherein m is a number from 0 to 20;
wherein R, $R_1$, $R_2$, $R_3$, and $R_4$ may be either straight chain or branched chain;
at least one block having a structure according to Formula III:

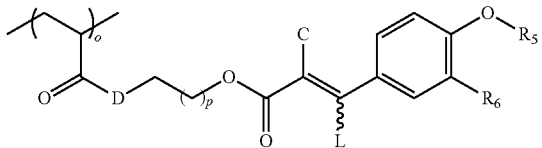

wherein:
$R_5$ is $C_1$-$C_{30}$ alkyl;
$R_6$ is selected from the group consisting of H and $C_1$-$C_{15}$ alkyl;
L is $C_1$-$C_{15}$ alkyl;
D is selected from the group consisting of O and S;
C is selected from the group consisting of CN and (C=O) NR$_7$ (R$_8$); and
each stereoisomer is selected from the group consisting of E, Z, R, S, and a combination thereof;
wherein $R_7$ and $R_8$ are independently $C_1$-$C_{15}$ alkyl;
wherein o is a number from 1 to 5,000;
wherein p is a number from 0 to 20;
wherein $R_5$, $R_6$, $R_7$ and $R_8$ are independently selected from $C_1$-$C_{15}$ alkyl;
at least one block having a structure according to Formula IV:

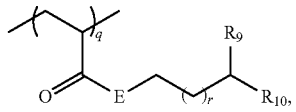

wherein:
$R_9$ and $R_{10}$ are independently $C_1$-$C_{15}$ alkyl, and
E is selected from the group consisting of O and S;
wherein q is a number from 1 to 5,000;
wherein r is a number from 0 to 20; and
at least one block has a structure according to Formula V:

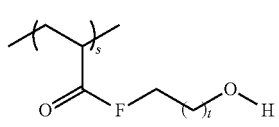

wherein:
F is selected from the group consisting of O and S;
wherein s is a number from 1 to 5,000; and
wherein t is a number from 0 to 20;
wherein the block copolymer is operable to quench the excited state energy; and
wherein the photoactive composition protects a substrate from oxidative stress caused by absorption of light having a wavelength in the wavelength range of about 280 nm to about 400 nm.

15. A method according to claim 14, wherein at least one block has a structure according to Formula VI:

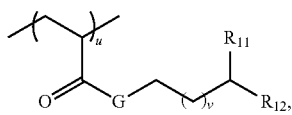

wherein:
$R_{11}$ and $R_{12}$ are independently $C_1$-$C_{15}$ alkyl, and
G is selected from the group consisting of O and S;
wherein u is a number from 1 to 5,000;
wherein v is a number from 0 to 20;
wherein $R_9$=$R_{10}$, or $R_{11}$=$R_{12}$, but not both.

16. A method according to claim 14, wherein the substrate comprises a sunscreen, a cosmetic, a polymer, and a coating.

17. A method according to claim 14, wherein application of said sunscreen to a skin of an animal thereby protects the skin against UV radiation.

18. A method according to claim 14, wherein the polymer comprises high-density polyethylene, low-density polyethylene, polystyrene, polyamides, nylon, polypropylene, rubber, cellulose, polyvinyl chloride, and polyvinyl alcohol.

19. A method according to claim 14, wherein the coating comprises stains, caulk, sealants, urethanes, enamels, films, adhesives, acrylic paints, latex paints, and inks.

20. A method according to claim 14, wherein the block copolymer is present at a concentration of about 1% by weight to about 20% by weight, based on a total weight of the composition.

21. A method according to claim 14, wherein the block copolymer is present at a concentration comprising about 15% by weight, about 10% by weight, about 5% by weight, about 1% by weight, or a combination thereof, based on the total weight of the composition.

22. A method according to claim 14, wherein the at least one photoactive compound comprises 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof; menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bis-benzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

23. A method according to claim 14, wherein the at least one photoactive compound is present at a concentration of about 0.000001% by weight to about 20% by weight, based on the total weight of the composition.

24. A method according to claim 14, wherein the at least one photoactive compound is present at a concentration comprising about 15% by weight, about 10% by weight, about 5% by weight, about 1% by weight, about 0.5% by weight, about 0.1% by weight, or a combination thereof, based on the total weight of the composition.

25. A method according to claim 14, wherein said photoactive composition includes an oil phase having a dielectric constant of at least about 7.

26. A method according to claim 14, wherein said photoactive composition includes an oil phase having a dielectric constant of at least about 8.

27. A method according to claim 13, wherein application of said cosmetic to a skin or a hair of an animal thereby protects the skin or hair against UV radiation.

28. A method according to claim 13, wherein application of said sunscreen to a skin of an animal thereby protects the skin against UV radiation.

29. A cosmetic or dermatological composition for coating a skin to protect the skin from oxidative stress caused by absorption of light having a wavelength in the wavelength range of about 280 nm to about 400 nm, the composition comprising:
(a) at least one photoactive compound that develops within itself an excited state energy when subjected to UV radiation,
(b) a block copolymer comprising a plurality of blocks, having a structure according to Formula I:

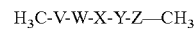

wherein the plurality of blocks comprises:
at least one block having a structure according to Formula II:

31

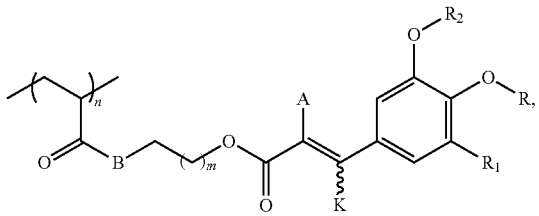

wherein:
R is $C_1$-$C_{30}$ alkyl;
$R_1$ is selected from the group consisting of H, OH, and $C_1$-$C_{15}$ alkoxyl;
$R_2$ is selected from the group consisting of H and $C_1$-$C_{15}$ alkyl;
K is $C_1$-$C_{15}$ alkyl;
B is selected from the group consisting of O and S;
A is selected from the group consisting of CN and (C=O) $NR_3$ ($R_4$); and
each stereoisomer is selected from the group consisting of E, Z, R, S, and a combination thereof;
wherein $R_3$ and $R_4$ are independently $C_1$-$C_{15}$ alkyl;
wherein n is a number from 1 to 5,000;
wherein m is a number from 0 to 20;
wherein R, $R_1$, $R_2$, $R_3$, and $R_4$ may be either straight chain or branched chain;
at least one block having a structure according to Formula III:

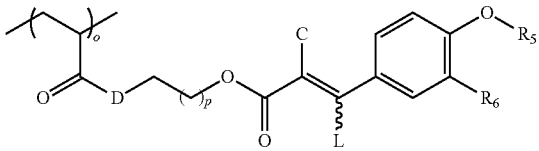

wherein:
$R_5$ is $C_1$-$C_{30}$ alkyl;
$R_6$ is selected from the group consisting of H and $C_1$-$C_{15}$ alkyl
L is $C_1$-$C_{15}$ alkyl;
D is selected from the group consisting of O and S;
C is selected from the group consisting of CN and (C=O)$NR_7$($R_8$); and
each stereoisomer is selected from the group consisting of E, Z, R, S, and a combination thereof;
wherein $R_7$ and $R_8$ are independently $C_1$-$C_{15}$ alkyl;
wherein o is a number from 1 to 5,000;
wherein p is a number from 0 to 20;
wherein $R_5$, $R_6$, $R_7$ and $R_8$ are independently $C_1$-$C_{15}$ alkyl;
at least one block having a structure according to Formula IV:

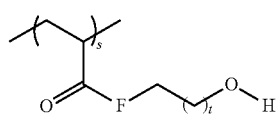

32 wherein:
$R_9$ and $R_{10}$ are independently $C_1$-$C_{15}$ alkyl, and
E is selected from the group consisting of O and S;
wherein q is a number from 1 to 5,000;
wherein r is a number from 0 to 20; and
at least one block having a structure according to Formula V:

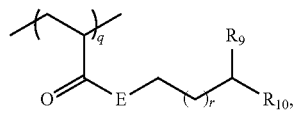

wherein:
F is selected from the group consisting of O and S;
wherein s is a number from 1 to 5,000;
wherein t is a number from 0 to 20;
wherein the block copolymer is operable to quench the excited state energy.

30. A cosmetic or dermatological composition of claim 29, wherein at least one block has a structure according to Formula VI:

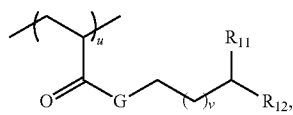

wherein:
$R_{11}$ and $R_{12}$ are independently $C_1$-$C_{15}$ alkyl, and
G is selected from the group consisting of O and S;
wherein u is a number from 1 to 5,000;
wherein v is a number from 0 to 20;
wherein $R_9$=$R_{10}$, or $R_{11}$=$R_{12}$, but not both.

31. A cosmetic or dermatological composition of claim 29, wherein the skin surface comprises human skin and animal skin.

32. A cosmetic or dermatological composition of claim 29, wherein the block copolymer is present at a concentration of about 1% by weight to about 20% by weight, based on a total weight of the composition.

33. A cosmetic or dermatological composition of claim 29, wherein the block copolymer is present at a concentration comprising about 15% by weight, about 10% by weight, about 5% by weight, about 1% by weight, or a combination thereof, based on the total weight of the composition.

34. A cosmetic or dermatological composition of claim 29, wherein the at least one photoactive compound comprises 4-methyldibenzoylmethane and derivatives thereof; octyl methoxycinnamate and derivatives thereof; octocrylene and derivatives thereof; p-methoxycinnamic acid esters and derivatives thereof; 1-(4-methoxyphenyl)-3-(4-tert-butylphenyl)propane-1,3-dione and derivatives thereof; oxybenzone and derivatives thereof; bis-ethylhexyloxyphenol methoxyphenyl triazone and derivatives thereof; methylene bis-benzotriazolyl tetramethylbutylphenol and derivatives thereof; 4-methylbenzylidene camphor and derivatives thereof; diethylamino hydroxyl benzoyl hexyl benzoate and derivatives thereof; drometrizole trisiloxane and derivatives thereof; ethylhexyl triazone, diethylhexyl butamido triazone and derivatives thereof; terephthalylidene dicamphor sulfonic acid, its salts, and derivatives thereof, menthyl anthranilate and derivatives thereof; retinol and derivatives thereof; coenzyme Q and derivatives thereof; cholecalciferol and derivatives thereof; porphyrin and derivatives thereof, resveratrol and derivatives thereof; p-aminobenzoic acid, its salts, and derivatives thereof; glyceryl esters; anthranilate and derivatives thereof; cinnamic acid and derivatives thereof, coumarin and derivatives thereof; trihydroxycinnamic acid and derivatives thereof; dibenzalacetone naphtholsulfonate, its salts, and derivatives thereof; dibenzalacetone and derivatives thereof; dihydroxy-naphthoic acid, its salts, and derivatives thereof; o-hydroxydiphenyldisulfonate, its salts, and derivatives thereof; diazole derivatives; quinine derivatives, its salts, and derivatives thereof; quinoline derivatives; hydroxyl-substituted benzophenone derivatives; quinolone derivatives; benzophenone derivatives; uric acid derivatives; quinine salts; hydroxydiphenyldisulfonate, its salts, and derivatives thereof; tannic acid and derivatives thereof; violuric acid and derivatives thereof; phenylbenzimidazole tetrasulfonate, its salts, and derivatives thereof; terephthalylidene dicamphor sulfonic acid, its salts, and derivatives thereof; benzalacetophenone naphtholsulfonate, its salts, and derivatives thereof; benzoic acid, its salts, and derivatives thereof; o-hydroxydiphenyldisulfonate, its salts, and derivatives thereof; p-naphthalate derivatives; methoxy-substituted uric acid derivatives; hydroquinone, its salts, and derivatives thereof; benzophenone derivatives; dihydroxycinnamic acid, its salts, and derivatives thereof; 1, 3, 5-triazine derivatives; methylene bisbenzotriazolyl tetramethylbutylphenol, its salts, and derivatives thereof; titanium dioxide and derivatives thereof; triazole and derivatives thereof; zinc oxide; bis-ethylhexyloxyphenol methoxyphenyl triazine and its salts; salicylate and derivatives thereof; diethylamino hydroxyl benzoyl hexyl benzoate, its salts, and derivatives thereof; and combinations of the foregoing.

35. A cosmetic or dermatological composition of claim 29, wherein the at least one photoactive compound is present at a concentration of about 0.000001% by weight to about 20% by weight, based on the total weight of the composition.

36. A cosmetic or dermatological composition of claim 29, wherein the at least one photoactive compound is present at a concentration comprising about 15% by weight, about 10% by weight, about 5% by weight, about 1% by weight, about 0.5% by weight, about 0.1% by weight, or a combination thereof, based on the total weight of the composition.

37. A cosmetic or dermatological composition of claim 29, wherein said composition includes an oil phase having a dielectric constant of at least about 8.

* * * * *